United States Patent [19]
Lipps

[11] Patent Number: 4,718,891
[45] Date of Patent: Jan. 12, 1988

[54] AUTOMATED HEMODIALYSIS CONTROL BASED UPON PATIENT BLOOD PRESSURE AND HEART RATE

[75] Inventor: Ben J. Lipps, Lafayette, Calif.

[73] Assignee: Henry Ford Hospital, Detroit, Mich.

[21] Appl. No.: 860,083

[22] Filed: May 6, 1986

Related U.S. Application Data

[63] Continuation of Ser. No. 606,707, May 3, 1984, abandoned.

[51] Int. Cl.[4] .............................................. A61M 1/03
[52] U.S. Cl. .............................. 604/31; 128/DIG. 13; 104/66; 104/67
[58] Field of Search .............. 128/DIG. 12, DIG. 13, 128/DIG. 3; 604/65, 66, 67, 4, 5, 6, 31

[56] References Cited

U.S. PATENT DOCUMENTS

| | | | |
|---|---|---|---|
| 3,946,731 | 3/1976 | Lichtenstein | 128/DIG. 13 X |
| 4,080,966 | 3/1978 | McNally et al. | 604/66 |
| 4,231,366 | 11/1980 | Schael | 604/4 |
| 4,392,849 | 7/1983 | Petre et al. | 604/66 |

FOREIGN PATENT DOCUMENTS 3223051  6/1982  Fed. Rep. of Germany.

OTHER PUBLICATIONS

Aver et al, "Microprocessor Control of Drug Infrin for Automatic Blood-Pressure Control", Med. & Biol. Eng & Comp., 3/81, pp. 171-174.

*Primary Examiner*—Edward M. Coven
*Attorney, Agent, or Firm*—Barnes, Kisselle, Raisch, Choate, Whittemore & Hulbert

[57] ABSTRACT

A method and system for continuously monitoring patient heart rate and blood pressure during hemodialysis and for automatically controlling fluid extraction rate and/or dialysate sodium concentration in the event that blood pressure and/or heart rate indicate onset or impending onset of a patient hypotensive episode. A decrease in patient blood pressure below preselected systolic and/or diastolic low alarm limits automatically initiates a second mode of therapeutic intervention wherein sodium concentration in the dialysate is increased for a predetermined time duration. Upon detection of such low blood pressure alarm, or upon detection of an increase in patient heart rate above a preselected alarm limit, the extraction rate of fluids from the patient through the ultrafiltration membrane is reduced in a first mode of therapeutic intervention by reducing such fluid extraction rate to a minimum level. Blood pressure and heart rate are thereafter monitored during this second mode of intervention to return ultrafiltration flow rate to its desired or goal level as blood pressure and heart rate indicate return of patient vital signs toward their initial levels.

2 Claims, 5 Drawing Figures

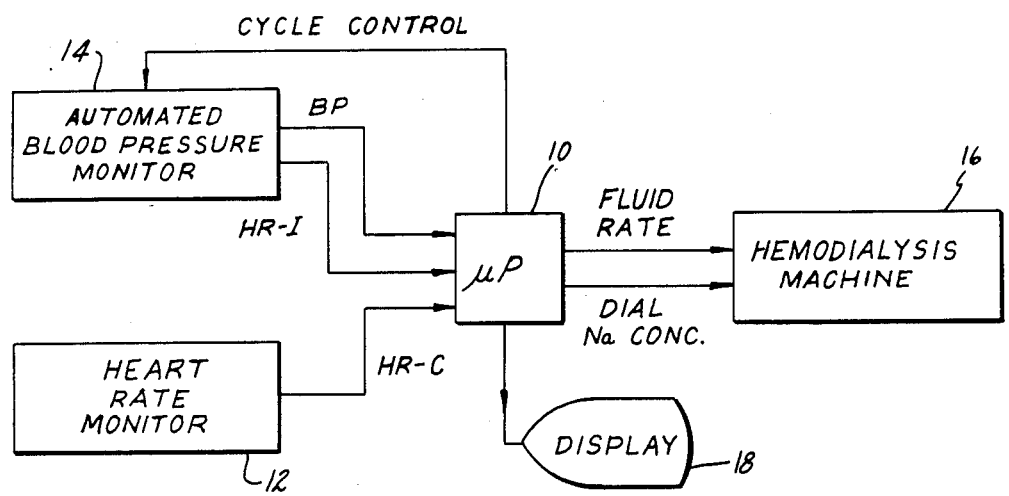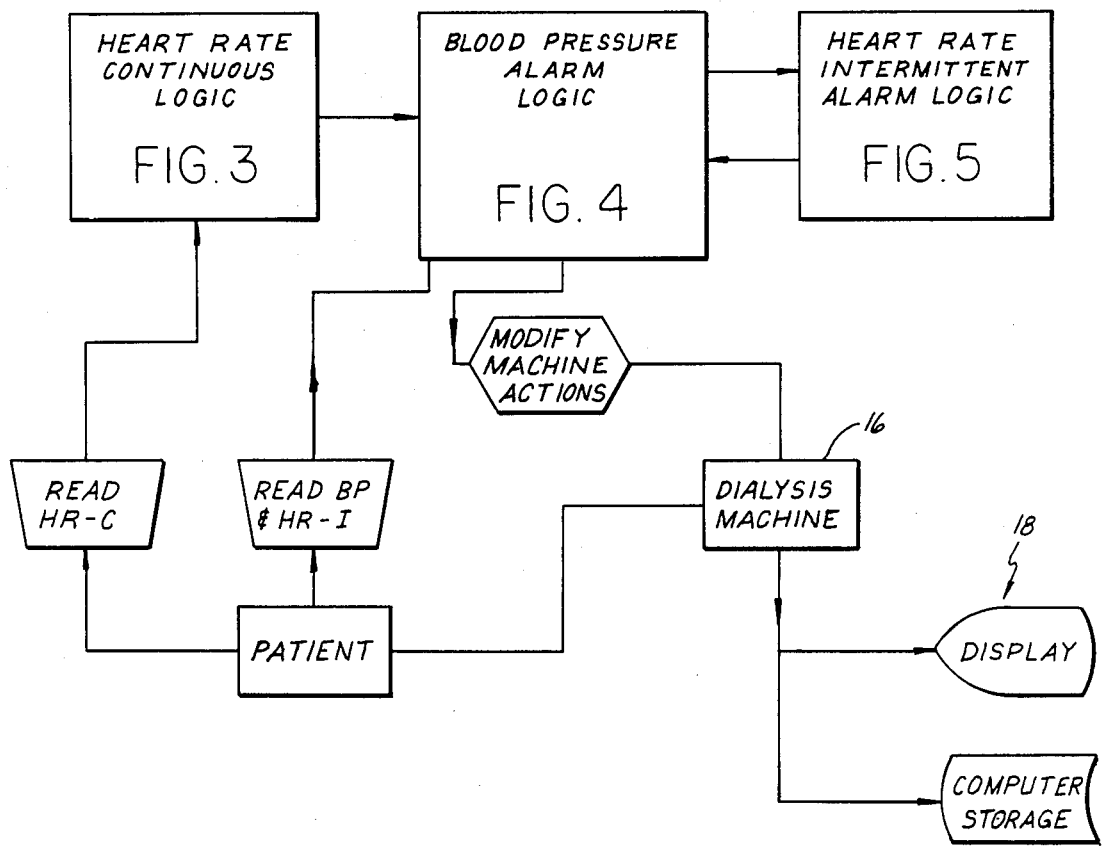

AUTOMATED HEMODIALYSIS CONTROL BASED UPON PATIENT BLOOD PRESSURE AND HEART RATE

This application is a continuation of application Ser. No. 606,707 filed May 3, 1984 and now abandoned The present invention is directed to controlled hemodialysis techniques, and more particularly to automated control of dialysate composition and/or patient fluid extraction rate to prevent patient hypotension.

BACKGROUND AND OBJECTS OF THE INVENTION

Hypotension during hemodialysis is a common occurrence, and results in significant patient discomfort and inefficient use of dialysis time and monitoring personnel. The causes of dialysis-related hypotension are several in origin, and in general result from an inability to increase peripheral resistance and cardiac output during hemodialysis. It has been the practice in the art to monitor the blood pressure of a dialysis patient, either manually or automatically, at periodic intervals and to initiate therapeutic intervention by monitoring personnel in the event of a hypotensive episode. If an episode occurs between monitoring intervals or is not detected by manual or automated blood pressure monitoring, the dialysis monitoring personnel are usually not aware of a potential problem until the patient has a massive reaction and exhibits substantial distress. In any event, the several maneuvers heretofore employed to manage and correct a hypotensive episode, including injection of sodium solution into the patient's bloodstream and/or reducing fluid extraction rate, require manual intervention by dialysis personnel and continued actual observation and monitoring of the patient until the episode is corrected. A high ratio of dialysis personnel to patients is therefore required.

It is therefore an object of the present invention to provide a fully automated method and apparatus for continuously monitoring patient vital signs during hemodialysis and automatically initiating therapeutic intervention upon occurrence of a hypotensive episode without requiring manual intervention by dialysis personnel.

Another and more specific object of the invention is to provide a method and system for detecting potential on-set of a hypotensive episode before the episode becomes actue by continuously monitoring patient vital signs, namely blood pressure and heart rate, and for automatically initiating therapeutic intervention to remedy the situation.

SUMMARY OF THE INVENTION

The present invention contemplates an automated blood pressure monitor for continuously reading or monitoring patient blood pressure at variable intervals selected by a control signal, an automated patient heart rate monitor for continuously monitoring patient heart rate during hemodialysis, and a hemodialysis machine which includes facility for separately controlling dialysate flow rate and sodium concentration. A programmed microprocessor is provided for controlling fluid extraction rate and dialysate sodium concentration, as well as blood pressure monitoring intervals, as a continuous and preselected function in real time of actual patient blood pressure and heart rate. Display and/or recording apparatus record patient vital signs and therapeutic intervention information for later analysis.

In accordance with one important aspect of the method and system of the present invention, decrease in patient blood pressure during dialysis below first systolic and/or diastolic alarm limits is detected to initiate a first alarm mode of operation and a first mode of therapeutic intervention. The hemodialysis machine is automatically controlled during such first intervention mode to increase sodium electrolyte concentration in the dialysate for a first predetermined time duration, specifically three minutes. (At the same time, fluid extraction rate is reduced from the desired or goal level initially set for the patient in question to a minimum flow rate, as will be described in detail hereinafter.) At the same time, the blood pressure monitoring cycle is controlled so as to obtain a further blood pressure reading following such dialysate sodium concentration control duration. If the patient's blood pressure remains below the systolic and/or diastolic low alarm limits, an audible alarm is activated to call for manual intervention by dialysis monitoring personnel. On the other hand, if the blood pressure systolic and diastolic readings have risen above the low alarm limits, a second intervention mode is entered for gradually returning dialysate pressure to the desired pressure for the patient in question.

In accordance with a second important aspect of the present invention, patient fluid extraction rate at the ultrafiltration membrane of the dialysis machine, which is also termed "ultrafiltration flow rate" or "UFR" in the present disclosure, is automatically controlled upon detection of an impending hypotensive episode and thereafter increased as a function of patient vital signs to a flow rate needed to obtain the total fluid extraction goal initially set for the patient in question. Specifically, upon detection of a decrease in blood pressure readings below the systolic and/or diastolic low alarm limits as previously described, or upon an increase in heart rate above a preselected high alarm limit, a second mode of therapeutic intervention is automatically initiated either concurrently with or separately from the first intervention mode, depending upon the reason for initiating the second intervention mode. Fluid flow rate across the ultrafiltration membrane is automatically reduced to a minimum flow rate level. Where the second intervention mode was entered concurrently with the first intervention mode because of a low blood pressure alarm, the automatic blood pressure monitoring interval is decreased so as to obtain blood pressure readings at greater frequency, specifically, every three minutes. When patient blood pressure has returned to 75% of its initial level, i.e. when dialysis was started, the ultrafiltration flow rate is automatically returned to 50% of the desired goal rate. If after a preselected time duration, specifically ten minutes, patient blood pressure is above the low alarm level, the ultrafiltration flow rate is returned to the rate necessary to obtain the desired fluid extraction goal. On the other hand, if the patient's blood pressure drops below the low alarm limits during such second intervention mode, the first and/or second intervention mode is reinitiated as is appropriate. If the second intervention mode was initiated by a high patient heart rate, ultrafiltration flow rate is returned to the goal level when heart rate falls below the high alarm limit.

In accordance with a third important aspect of the present invention, both heart rate and blood pressure are monitored and compared with initial patient readings obtained when dialysis began so as to detect potential onset of a hypotensive episode. In particular, both blood pressure and heart rate are compared to the initial readings to initiate a third mode of intervention when either blood pressure or heart rate deviates from the initial readings by more than preselected deviation limits, specifically plus or minus thirty mmHg in the case of blood pressure and plus or minus twenty bpm in the case of heart rate. In such third mode of intervention, the frequency of obtaining blood pressure readings is increased by suitably controlling the automated blood pressure monitoring operation. When blood pressure and heart rate have returned to levels within the deviation limits, the frequency of obtaining blood pressure readings is returned to its initial level, typically on the order of every twenty minutes.

Blood pressure alarm situations always take precedence over potential heart rate alarm situations in accordance with the present invention, which means for example that a blood pressure reading below the low systolic or diastolic alarm limit will automatically initiate both the first and second modes of intervention regardless of heart rate readings. It is likewise preferred in accordance with the invention to initiate the first mode of operation no more than four times during a four-hour dialysis interval. If the first mode of intervention is called for more than four times during a four-hour dialysis interval, an alarm is activated to notify monitoring personnel.

BRIEF DESCRIPTION OF THE DRAWINGS

The invention, together with additional objects, features and advantages thereof, will be best understood from the following description, the appended claims and the accompanying drawings in which:

FIG. 1 is a functional block diagram of a presently preferred embodiment of an automated hemodialysis control system in accordance with the invention;

FIG. 2 is a chart which illustrates in general or summary form flow of information in the system illustrated in FIG. 1.

DETAILED DESCRIPTION

Figure 4:
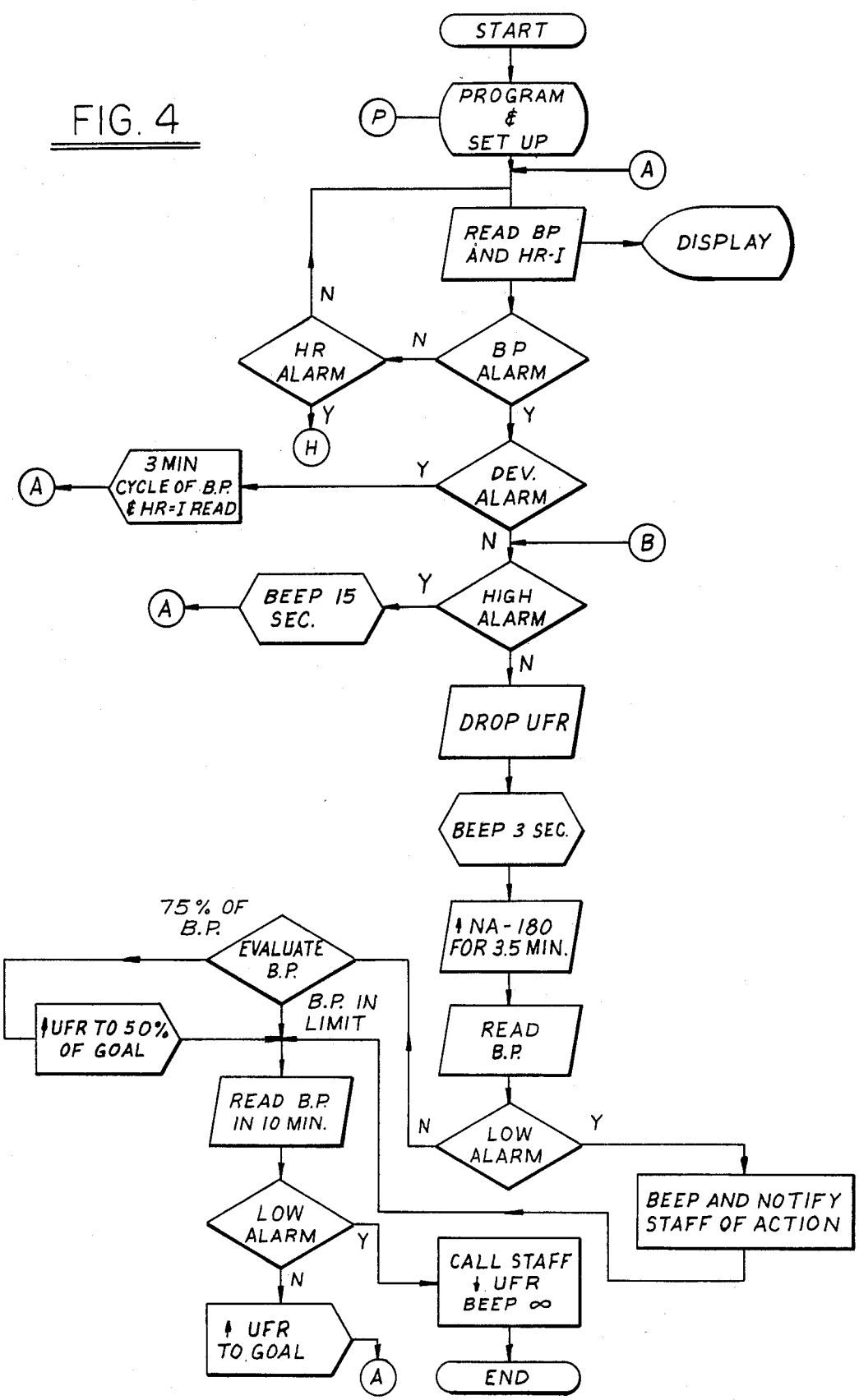
FIGS. 3-5 are detailed information flow charts of subroutines illustrated in block form in FIG. 2.

FIG. 1 is a functional block diagram of the invention which illustrates a microprocessor 10 receiving a continuous pulsed heart rate signal HR-C from a monitor 12. Microprocessor 10 also receives an intermittent heart rate signal HR-I and a blood pressure signal BP from an automated blood pressure monitor 14, and provides a control signal to monitor 14 for controlling the frequency of obtaining blood pressure and intermittent heart rate-signals therefrom. In a working embodiment of the invention, heart rate monitor 12 comprises a conventional Model 7719 infrared monitor marketed by Computer Instruments, Inc. of N.Y. and adapted to be attached to the ear lobe of a dialysis patient for providing a continuing series of pulsed signals indicative of heart or pulse rate. Automated blood pressure monitor 14 comprises a Bard automated Sentron monitor marketed by Bard Biomedical Division of Lombard, Ill. It has been found that sufficient memory is available in this particular monitor that microprocessor 10 may be physically included therein rather than provided as a separate unit.

A conventional automated hemodialysis machine 16 is connected to receive control signals from microprocessor 10. Machine 16 conventionally includes an ultrafiltration membrane and pumps for circulating a dialysate and patient blood along opposite sides of the membrane. Machine 16 further includes suitable input controls which may be preset by a nurse for establishing a goal or target quantity of fluid to be removed from the dialysis patient during the dialysis period. Internal control logic automatically regulates the flow of dialysate past the membrane for obtaining the desired fluid extraction goal. Machine 16 also includes a suitable apparatus for measuring conductivity of the dialysate, and circuitry for controlling addition of a sodium electrolyte solution from a reservoir to the dialysate to obtain a desired conductivity. Ultrafiltration flow rate and sodium concentration are thus normally controlled by circuitry internal to machine 16 in the absence of control signals from microprocessor 10. In the working embodiment of the invention identified above, dialysis machine 16 comprises a Seratron machine marketed by Seratronics Inc. of Concord, Calif. Microprocessor 10 is also connected to suitable display and/or storage means 18 for storing and/or displaying patient and intervention data, and for notifying the monitoring personnel of the various alarm conditions.

In the following description, the terms "heart rate continuous" and "heart rate intermittent" are employed relative to the signals HR-C and HR-I in FIG. 1. A typical blood pressure monitoring machine, of which the Seratron machine is exemplary, includes facility for measuring heart rate when a blood pressure reading is taken. Because microprocessor 10 is physically included in blood pressure monitor 14 in the working embodiment of the invention heretofore described, it is advantageous to employ the heart rate signal obtained by the blood pressure monitor when available. Because the signal is only available where a blood pressure reading is taken, it is termed "intermittent" in the description. The "continuous" heart rate signal from monitor 12 is employed to detect potential onset of a hypotensive episode between blood pressure readings. It will be understood, however, that use of the "intermittent" heart rate signal takes precedence over the HR-C readings, which are used to modify the frequency of BP cycles, and that the "continuous" heart rate signal could be used throughout.

Before proceeding with the detailed description of the control process, the various alarm limits and alarm modes of operation will be outlined. Microprocessor 10 (FIG. 1) is preprogrammed with high and low blood pressure and heart rate alarm limits which may be modified from an operator control panel (not shown) but to which the processor logic defaults in the absence of operator limit programming. For blood pressure, the preprogrammed high systolic alarm limit is 200 mmHg and the high diastolic alarm limit is 120 mmHg. The preprogrammed low systolic limit is 90 mmHg and the low diastolic alarm limit is 50 mmHg. The preprogrammed high heart rate alarm limit is 120 bpm and the low alarm limit is 40 bpm. In addition to these high and low alarm limits, microprocessor 10 is further preprogrammed to detect deviation of heart rate and blood pressure from initial readings obtained and stored at the onset of dialysis, and to initiate control action when heart rate or blood pressure deviates from the initial readings by more than preselected amounts. The preprogrammed blood pressure deviation limit is ±30 mmHg and the heart rate deviation limit is ±20 bpm. All of these preprogrammed limits may be modified by operator intervention. Microprocessor 10 is initially programmed to obtain blood pressure and intermittent heart rate readings every 20 minutes during the hemodialysis process. Upon detection of an alarm condition in either the first or second alarm modes of operation, the frequency of obtaining the intermittent heart rate and blood pressure signals is controlled as will be described in the following discussion.

Dialysis machine 16 is initially preset by an operator to extract a desired or "goal" fluid volume from the patient during a preselected dialysis treatment period, such as four hours. Machine 16 includes internal circuitry which may automatically regulate dialysate flow rate as a function of the amount of treatment time remaining to obtain the desired fluid extraction goal. In the event of therapeutic intervention in accordance with the invention, the internal circuitry of machine 16 will automatically reset ultrafiltration flow rates after intervention to obtain the desired goal. Likewise, machine 16 includes internal means for measuring dialysate sodium concentration as a function of dialysate conductivity, and to control such concentration automatically.

FIG. 2 illustrates overall information flow in the system of FIG. 1. A heart rate-continuous subroutine receives continuous heart rate signals from the patient by means of heart rate monitor 12 (FIG. 1). A blood pressure alarm logic subroutine receives a first input from the heart rate-continuous subroutine, and also receives blood pressure and intermittent heart rate signals from the patient by means of blood pressure monitor 14 (FIG. 1). The intermittent heart rate signal HR-I is fed to a heart rate-intermittent alarm logic subroutine for analysis. The blood pressure alarm logic subroutine, which is the main processor subroutine, detect alarm conditions and, in various alarm modes of operation, modifies operation of dialysis machine 16 which in turn affects the patient. The control action of the blood pressure monitor alarm logic is also fed to display and/or storage 18. The heart rate-continuous, blood pressure alarm logic and heart rate-intermittent alarm logic subroutines are illustrated in greater detail in FIGS. 3, 4 and 5 respectively.

Figure 3:
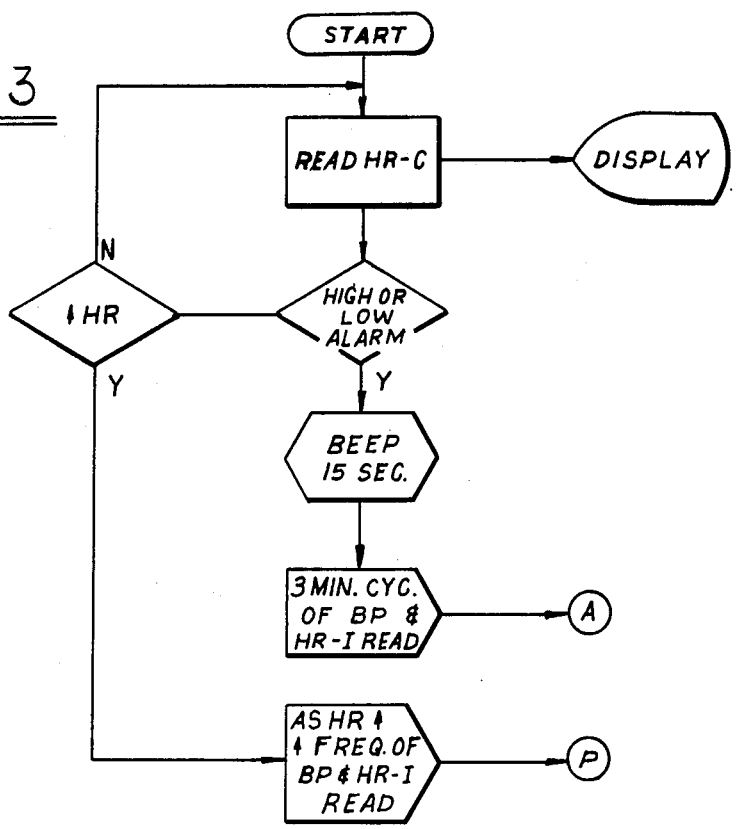

Turning now to FIG. 3, the heart rate signal HR-C from monitor 12 (FIG. 1) is continuously read and fed to operator display 18. At the same time, the continuous heart rate signal is monitored for a high or low alarm condition as previously described. In the absence of an alarm condition, the logic continues in a closed loop. However, the heart rate frequency is continuously monitored and, if the heart rate is detected to be increasing, the frequency of BP and HR-I readings is correspondingly increased. In the event of detection of a limit alarm, an operator alarm buzzer is "beeped" for 15 seconds, the blood pressure cycle control circuitry is reset to obtain blood pressure and intermittent heart rate information every three minutes, and the subroutine branches to point A in the blood pressure alarm logic subroutine of FIG. 4.

Turning to FIG. 4, blood pressure information BP and intermittent heart rate information HR-I are intermittently read either under programmed control or upon occurrence of a limit alarm condition detected in the heart rate continuous logic of FIG. 3. The programmed BP and HR-I may be under preprogrammed default control or operator-set control, and may be modified by increasing heart rate per FIG. 3. In any event, blood pressure information BP and intermittent heart rate information HR-I are displayed when readings are taken. At the same time, the blood pressure signal BP and the intermittent heart rate signal HR-I are each tested for an alarm condition. Such alarm condition may be either a high/low alarm condition or a deviation alarm condition, as previously described. If a heart rate alarm condition is detected but no blood pressure alarm condition is detected, the control logic branches to point H in the heart rate intermittent alarm logic of FIG. 5. However, if a blood pressure alarm condition is detected, either a deviation alarm or a limit alarm, the blood pressure alarm logic retains control. That is, detection of a blood pressure alarm of any type takes precedence or priority over a heart rate alarm. If neither a BP alarm nor an HR alarm is detected, the logic recycles to form the main loop of the flow diagrams.

Continuing within the blood pressure alarm logic of FIG. 4, a blood pressure signal which initiates the alarm indication is tested for alarm type. If the alarm is a deviation-type alarm, which means that the systolic or diastolic reading deviates from the patient's initial reading by more than a deviation limit, the blood pressure and intermittent heart rate monitoring cycle is decreased from the programmed normal cycle time (20 minute default value) to a three-minute monitoring cycle, and the control logic is returned to point A for the next reading of blood pressure and intermittent heart rate information. If the blood pressure alarm indication does not result from a deviation alarm, which means that the blood pressure alarm is a limit-type alarm, the limit alarm is tested to determine whether the high or low limit has been passed. Again, both the systolic and diastolic readings are tested. If the limit alarm is a high-type limit alarm, which means that either the diastolic or the systolic reading exceeds the associated programmed or default high alarm limit, the operator alarm is "beeped" for 15 seconds and the control logic is returned to point A. However, if the blood pressure limit alarm is not of the high alarm type, which means that the alarm is a low alarm indicating onset of a hypotensive episode, therapeutic intervention is immediately initiated in both intervention modes one and two.

As a first intervention step, the extraction fluid flow rate through the ultrafiltration membrane is decreased to a minimum level, which is 50 ml/hr in the particular dialysis machine of the working example herein discussed. At the same time, dialysate sodium concentration is increased to 180 meq/l for a period of three minutes, after which sodium concentration is dropped to the normal level of 140 meq/l. Following this preprogram three minute interval, blood pressure is again read and tested for a low alarm condition. If the low alarm condition persists, the dialysis operation is terminated and the dialysis monitoring staff is alerted by a continuous beeping alarm signal. On the other hand, if the blood pressure has increased above the low alarm limits following therapeutic intervention by dialysate sodium concentration increase and ultrafiltration flow rate decrease, the blood pressure signal is evaluated in comparison with its original level. If the blood pressure level (both systolic and diastolic) has returned to within 75% of its initial level, the ultrafiltration flow rate is increased to 50% of the level necessary to obtain the fluid extraction goal initially set by the operator. On the other hand, if the blood pressure is above the low limits but not within 75% of initial levels, UFR remains at xinimum level. In either event, blood pressure is again read after ten minutes. If blood pressure is now above the low alarm level, UFR is increased to the level necessary to obtain the desired fluid extraction goal within the dialysis time remaining, and the control logic is returned to point A so as to function within the main control loop. However, if the blood pressure reading after the ten minute interval is again below the low alarm levels, the control subroutine branches to point E which terminates the dialysis operation and alerts the monitoring staff.

Figure 5:
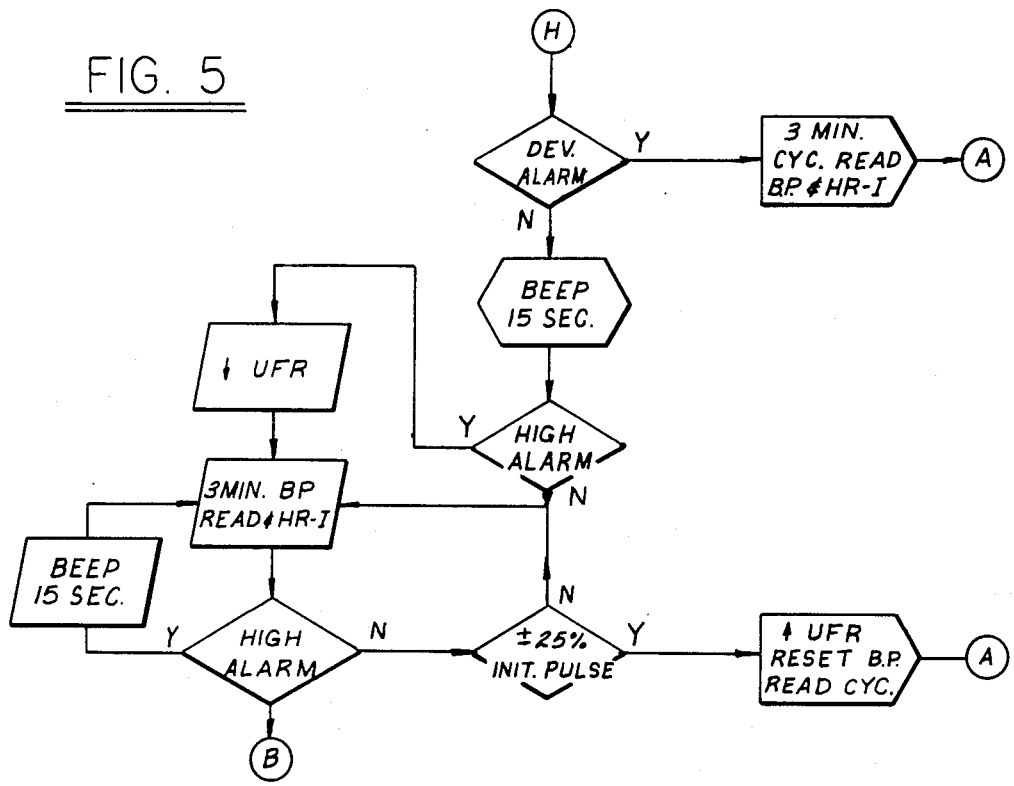

FIG. 5 illustrates the heart rate alarm logic subroutine which becomes operative upon detection of a heart rate alarm condition per FIG. 4 as previously described and branching of the control logic to point H. The heart rate alarm condition is first tested to determine alarm type. If the alarm type is a deviation alarm, indicating that the intermittent heart rate signal has deviated by more than preselected limits from the initial heart rate signal, the blood pressure and intermittent heart rate read cycle is reset to three minutes, and the control logic is returned to point A at the main loop in FIG. 2. On the other hand, if the intermittent heart rate alarm signal is not a deviation-type alarm, which means that the alarm is a lixit-type alarm, the staff alarm is "beeped" for 15 seconds and the heart rate information is tested to determine whether a low or high alarm is indicated. If a low alarm is indicated, the cycle time for monitoring blood pressure and intermittent heart rate is reset to three minutes, and the control logic returns to point A. On the other hand, if a high heart rate alarm condition is indicated, which means that the intermittent heart rate signal exceeds the preselected high alarm limit (either preset or default), the ultrafiltration flow rate is decreased to its minimum level and intermittent heart rate and blood pressure are again read in three minutes. If the high intermittent heart rate alarm condition persists, the ultrafiltration rate remains low, and blood pressure and intermittent heart rate are continuously read every three minutes. On the other hand, if the high heart rate alarm condition terminates following therapeutic intervention in the form of decreased ultrafiltration flow rate, the ultrafiltration flow rate is returned to its goal level and the control cycle returns to the primary loop at point A. It must be borne in mind in connection with FIG. 5 that, if any of the reading operations wherein blood pressure and intermittent heart rate are monitored indicates a blood pressure alarm condition, control is immediately returned to the blood pressure alarm logic of FIG. 4 because a blood pressure alarm condition always takes precedence over a heart rate alarm condition in accordance with the principles of the present invention.

The invention claimed is:

1. A method of controlling hemodialysis as a continuous function of vital signs of a patient connected to a hemodialysis machine which includes means for controlling dialysate composition and rate of fluid extraction from the patient, said method comprising the steps of:
   (a) intially maintaining sodium electrolyte concentrations in said dialysate at 140 meq/l,
   (b) intermittently sampling patient blood pressure at predetermined first sample intervals,
   (c) detecting decrease in patient blood pressure below a first alarm limit to initiate a first alarm mode of operation and provide a first alarm signal, and
   (d) responsive to said first alarm signal, automatically increasing sodium electrolyte concentration in said dialysate to 180 meq/l for a first predetermined time duration, and thereafter reducing said concentration to 140 meq/l.

2. The method set forth in claim 1 comprising the additional steps of:
   (e) responsive to said first alarm signal, automatically sampling patient blood pressure after said first time duration, and
   (f) providing a second alarm signal if patient blood pressure remains below said first alarm limit.

* * * * *